United States Patent [19]

Roth et al.

[11] Patent Number: 5,451,205
[45] Date of Patent: Sep. 19, 1995

[54] FACILITATED OXYGEN DELIVERY IN CONJUNCTION WITH HEMODILUTION

[75] Inventors: Duane J. Roth, La Jolla; Peter E. Keipert, San Diego, both of Calif.; Nicholas S. Faithfull, The Woodlands, England; Thomas F. Zuck, Cincinnati, Ohio; Jean G. Riess, Nice, France

[73] Assignee: Alliance Pharmaceutical Corp., San Diego, Calif.

[21] Appl. No.: 253,414

[22] Filed: Jun. 3, 1994

Related U.S. Application Data

[63] Continuation of Ser. No. 843,518, Feb. 28, 1992, Pat. No. 5,344,393.

[51] Int. Cl.$^6$ ............................................. A61K 47/00
[52] U.S. Cl. ......................................... 604/6; 514/532
[58] Field of Search ...................... 424/5; 604/4, 5, 6, 604/19, 27, 28, 48, 59, 56

[56] References Cited

U.S. PATENT DOCUMENTS

| | | |
|---|---|---|
| 3,482,575 | 12/1969 | Claff et al. |
| 3,975,512 | 8/1976 | Long |
| 4,073,879 | 2/1978 | Long, Jr. |
| 4,275,726 | 6/1981 | Schael |
| 4,301,144 | 11/1981 | Iwashita et al. |
| 4,473,494 | 9/1984 | Tye |
| 4,526,715 | 7/1985 | Kothe et al. |
| 4,600,531 | 7/1986 | Walder |
| 4,698,387 | 10/1987 | Schmidt et al. |
| 4,777,244 | 10/1988 | Bonhard et al. |
| 4,861,867 | 8/1989 | Estep |
| 4,911,929 | 3/1990 | Farmer et al. |
| 4,927,623 | 5/1990 | Long, Jr. |
| 4,963,130 | 10/1990 | Osterholm |
| 4,981,691 | 1/1991 | Osterholm et al. |
| 4,987,154 | 1/1991 | Long, Jr. |
| 5,080,885 | 1/1992 | Long, Jr. |
| 5,130,230 | 7/1992 | Segall et al. |

FOREIGN PATENT DOCUMENTS 0231070 8/1987 European Pat. Off.

OTHER PUBLICATIONS

Faithfull, N. S. et al., Peripheral vascular responses to fluorocarbon administration, *Microvascular Research* 33:183-193 (1987).

Faithfull, N. S. et al., Critical levels of O$_2$ extraction following hemodilution with dextran of fluosol-DA. *J of Critical Care* 3(1): 14-18 (1988).

Federspiel, W. J. et al., A theoretical analysis of the effect of the particulate nature of blood on oxygen release in capillaries. *Microvascular Research* 32: 164-189 (1986).

Fukushima, K. et al., Clinical experience of hemodilution with fluosol-DA. *Jpn. J. Anesthesiol.* 30(7): 741-745 (with abstract & translation) (1981).

Giordano, G. F. et al., An autologous blood program coordinated by a regional blood center: a 5-year experience. *Transfusion* 31(6): 509-512 (1991).

Gould, S. A. et al., Fluosol-DA as a red-cell substitute in acute anemia. *New Engl. J. Med.* 314: 1653-1656 (1986).

Greenwalt, et al., Perioperative red blood cell transfusion. *JAMA* 260(18): 2700-2703 (1988).

(List continued on next page.)

*Primary Examiner*—Sam Rimell
*Attorney, Agent, or Firm*—Knobbe, Martens, Olson & Bear

[57] ABSTRACT

A method for facilitating autologous blood use by a patient facing a loss of blood, comprising the steps of removing and preferably storing a portion of the patient's blood, intravenously administering a biocompatible liquid in sufficient quantity to substantially maintain the patient's hemodynamic stability, wherein the liquid comprises an effective oxygen-delivery enhancing amount of a biocompatible synthetic oxygen carrier, after which the patient undergoes a loss of blood, and then readministering blood to the patient, preferably the stored blood. In one embodiment, the biocompatible liquid further comprises a hemodiluent and the hemodiluent is administered separately from the oxygen carrier.

20 Claims, 6 Drawing Sheets

OTHER PUBLICATIONS

Gutierrez, G., The rate of oxygen release and its effect on capillary $O_2$ tension: a mathematical analysis. *Respiration Physiology* 63: 79–96 (1986).

Homer, L. D. et al., Oxygen gradients between red blood cells in the microcirculation. *Microvascular Research* 22: 308–323 (1981).

Mercuriali, F. et al., A safe alternative for surgical patients. *Autologous Blood* 2-30 (1991).

Messmer, K. et al., Present state of intentional hemodilution. *Eur. surg. Res.* 18: 254–263 (1986).

Messmer, K. et al., Oxygen supply to the tissues during limited normovolemic hemodilution. *Res. exp. Med.* 159: 152–166 (1973).

Riess, J. G., Overview of progress in the fluorocarbon approach to in vivo oxygen delivery. *Biomat., Art. Cells & Immob. Biotech.* 20(2-4): 183–202 (1992).

Riess, J. G. et al., Design, synthesis and evaluation of fluorocarbons and surfactants for in vivo applications new perfluoralkylated polyhydroxylated surfactants. *Int'l Symposium on Blood Substitutes*, Montreal (1987).

Riess, J. G., Reassessment of criteria for the selection of perfluorochemicals for second-generation blood substitutes: analysis of structure/property relationships. *Artificial Organs* 8(1): 44–56 (1984).

Riess, J. G., Fluorocarbon-based in vivo oxygen transport and delivery systems. *Vox Sang* 61: 225–239 (1991).

Sheffield, C. et al., Preparation and in vivo evaluation of two bovine hemoglobin-based plasma expanders. *Biotechnol. Appl. Biochem.* 12(6): 630–642 (1990).

Stehling, L. et al., Acute normovolemic hemodilution. *Transfusion* 31(9): 857–868 (1991).

Winslow, R. M., A model for red cell $O_2$ uptake. *International J. of Clinical Monitoring and Computing* 2: 81–93 (1985).

Zauder, H. L., Preoperative hemoglobin requirements. *Hemorrhagic Disorders* 8(3): 471–480 (1990).

Zuck, T. F. et al., Autologous transfusion practice. *Vox Sang* 58: 234–253 (1990).

FACILITATED OXYGEN DELIVERY IN CONJUNCTION WITH HEMODILUTION

This application is a continuation of application Ser. No. 07/843,518, filed Feb. 28, 1992, U.S. Pat. No. 5,344,393.

BACKGROUND OF THE INVENTION

The present invention relates to improved medical procedures in which addition of a synthetic oxygen carrier in connection with autologous blood replacement (and, preferably, in connection with hemodilution) is used to reduce or eliminate the need for homologous blood.

More than 13 million units of blood are collected each year in the United States alone, and about 10 million of these units are transfused into 4 million recipients. Of the transfused units, about two-thirds are used during surgical procedures, and the remainder are used primarily for treating severe anemia or in emergency indications. Experience from clinical studies suggests that postoperative recovery can be shortened if hemoglobin concentrations are not allowed to fall to below 10 g/dL, the generally accepted indication for transfusion (Zauder, Anesth. Clin. North Amer 8:471-80 (1990)). This criterion, however, is currently being reevaluated due in part to a recent increase in awareness of the risks associated with homologous blood transfusion (NIH Consensus Conference JAMA 260:2700-2703 (1988)). This has also resulted in a renewed interest in the use of autologous blood transfusion techniques, in particular predonation and acute normovolemic hemodilution (ANH).

Although autologous blood transfusion (i.e., reinfusion of the patient's own blood) was first employed over 170 years ago, it was not until the early 1970s that its use became more widespread because of growing concerns about the transmission of hepatitis. More recently, interest in autologous transfusions on the part of both patients and physicians has been stimulated by the emergence of AIDS. Despite an increased awareness and acceptance of the benefits of autologous blood transfusion, recent studies have revealed the widespread underutilization of autologous predonation (which is estimated to represent only 2-5% of all units drawn nationwide).

The outcome of some surgical procedures may be improved by reducing blood viscosity prior to surgery. This can be accomplished with ANH at the start of an operation (Stehling et al. Transfusion 31:857 (1991)). ANH is a procedure whereby several units of blood are withdrawn from the patient at the beginning of surgery and simultaneously replaced with either a crystalloid or a colloid plasma volume expander. The basic mechanism that compensates for most of the decreased oxygen capacity of the diluted blood is the rise in cardiac output and increased organ blood flow, factors that result from the improved fluidity of blood (i.e., lower viscosity) at lower hematocrit levels (Messmer et al Eur. Surg. Res. 18:254-263 (1986)).

Predonation typically involves withdrawal of several units of a patient's blood during the six weeks prior to surgery. To avoid excessive anemia, the amount of blood that can be safely predonated in the weeks before surgery is limited, as is the amount of blood that can be removed during ANH.

One potential drawback of ANH and, to a lesser degree, predonation, is the loss of oxygen carrying capacity of the blood during surgery.

Quite apart from ANH and predonation, it has been suggested that red cell substitutes, or blood substitutes, could be used in place of homologous blood (i.e., blood from other humans) during surgery. Extensive research in the field of such blood substitutes over the past two decades has resulted in several candidate compositions. These include perfluorocarbon emulsions, such as Fluosol ™ (Green Cross Corporation, Japan) and Oxygent ™ (Alliance Pharmaceutical Corp., San Diego, USA), and hemoglobin compositions, such as those derived from human, animal, or recombinant sources. Traditional thinking has been that a red cell substitute would be given in volumes equal to the amount of whole blood that would be used for the same purpose.

Unfortunately, the use of such blood substitutes to replace blood used in transfusions has not been entirely satisfactory. Early studies using Fluosol, for example, as a blood substitute found that after blood loss, fluosal was "unnecessary in moderate anemia and ineffective in severe anemia." Gould, et al., New Engl. J. Med. 314:1653 (1986). In this study, the average increase in arterial oxygen content with the drug was only 0.7 ml/deciliter. Thus, it was believed that use of such fluorocarbon emulsions as blood substitutes would not provide a significant benefit in severely anemic patients. Indeed, although the U.S. Food & Drug Administration has now approved Fluosol for use as a perfusion agent during percutaneous transluminal coronary angioplasty (PTCA), it has to date refused to approve its use as a blood substitute for general use.

Another problem in using fluorocarbon emulsions and hemoglobin compositions as red cell substitutes or blood substitutes to compensate for blood loss from surgery, disease, or trauma is the relatively short half life of those materials in vivo. Healthy humans typically require about two weeks to manufacture new red cells and increase hematocrit to normal following blood loss. In contrast, the intravascular half life of fluorocarbon emulsions and hemoglobin substitutes in vivo is typically less than 72 hours, often less than 24 hours. Thus, even if sufficient quantities of a red cell substitute are administered during and/or after surgery, for example, to provide adequate oxygen delivery, the oxygen carrying capacity will drop significantly long before the body can compensate by making new red cells.

SUMMARY OF THE INVENTION

The present invention includes a method for facilitating autologous blood use by a patient facing a loss of blood, comprising the steps of removing and preferably storing a portion of the patient's blood, intravenously administering a biocompatible liquid in sufficient quantity to substantially maintain the patient's blood volume, wherein the liquid comprises an effective oxygen-delivery enhancing amount of a biocompatible oxygen carrier, after which the patient undergoes a loss of blood, and then readministering blood to the patient, preferably the stored blood. In one embodiment, the biocompatible liquid further comprises a hemodiluent and the hemodiluent is administered separately from the oxygen carrier. Although the invention includes oxygen carriers derived from human, animal, plant, or recombinant hemoglobin, the preferred oxygen carrier is a fluorocarbon emulsion. In that embodiment, the volume of the administered oxygen carrier is advantageously less than about 50% of the volume of the hemodiluent. The fluorocarbon emulsions may have concentrations as low as 5% or 10%, w/v, but preferably have a concentration of at least 40% or 60%, w/v. In some embodiments, the hemodiluent is a crystalloid, a colloid, or a combination thereof. A preferred aspect of the invention includes administering oxygen breathing gas to the patient during performance of the method. The blood loss contemplated by the present invention includes blood loss from surgery, trauma, or disease. Although the precise amount of administered oxygen carrier will vary, general preferred ranges are between about 0.5 and 10 ml/kg, based on the body weight of the patient.

The invention further includes use of a non-blood oxygen carrier in the preparation of a medicament for use in the foregoing method, or for use during hemodilution of a patient, particularly when the hemodilution and administration of the oxygen carrier is followed by transfusion of whole blood or red cells, preferably an autologous transfusion.

DETAILED DESCRIPTION OF THE INVENTION

A. Overview of the Invention

Figure 1:
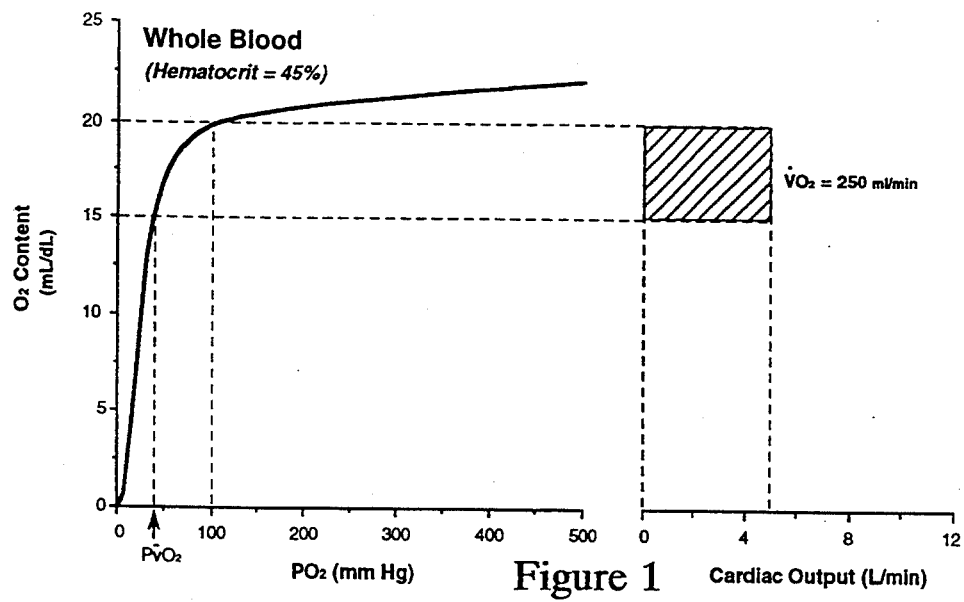
FIG. 1 is a graph showing the relationship between the $O_2$ delivery from hemoglobin in blood and the cardiac output under normal conditions (hematocrit=45%). Total $O_2$ utilization (or consumption; $VO_2$) is equal to the product of cardiac output times the arterial-venous $O_2$ content difference, and has been indicated by the cross-hatched area. OxyHb dissociation curves were generated from data provided by the model developed by Winslow, Int. J. Clin. Monitor Comp. 2:81–93 (1985)).

The invention described below combines the use of limited intravascular half-life oxygen carriers (blood substitutes) with autologous blood transfusion strategies, including in particular, a combination of predonation and perioperative hemodilution. In patients who have donated blood prior to surgery (predonation) and for whom concerns about adequate oxygen-carrying capacity remain, an oxygen carrier can be infused. An additional margin of safety with respect to enhanced oxygen delivery will be provided with such a supplementation. Small amounts of the substitute, typically not approaching one-to-one (i.e. not equal volume) replacement, would be effective in providing this margin of safety.

As an alternative, an oxygen-carrying blood substitute with limited intravascular persistence can be used as a partial replacement formulation during perioperative hemodilution. As above, this supplementation need not be a one-to-one replacement for the volume of blood withdrawn during or after hemodilution, but is rather to supplement the oxygen-carrying capacity during or after hemodilution with crystalloid and/or colloid-based solutions. In this clinical situation an additional margin of safety is afforded to the hemodiluted patient, by augmenting total oxygen delivery.

Two unique features of the present invention are of particular importance. First, the invention represents a departure from use of blood substitutes as replacements for blood in acute or chronic anemia on a one-to-one basis. Instead, the present invention increases the margin of safety of existing autologous transfusion technologies, preferably through less that one-to-one replacement that is, by smaller volume infusion of an oxygen carrier (blood substitute). The present invention includes the discovery that a small volume of an oxygen carrier will be efficacious by providing the benefit of enhanced oxygen delivery, particularly when used in combination with autologous transfusion techniques. This hypothesis has been confirmed in a dog model of acute hemodilution.

Second, the combined use of autologous and blood substitute infusion technologies to avoid homologous transfusion is emphasized. The present invention contemplates use of both predeposit and perioperative autologous technologies with preferably less that one-to-one infusions of various oxygen-carrying blood substitute formulations. This invention includes use of any or all of these technologies in whatever order or of whatever magnitude they may be clinically useful in the perioperative clinical setting described.

B. Materials

A large number of materials suitable for use in the present invention are already known in the art. Without limiting the scope of the invention, certain representative materials are discussed below.

Several compositions have been proposed or demonstrated to function as intravenous oxygen carriers. These include fluorocarbon emulsions, including but not limited to perfluorocarbon emulsions. Such emulsions are typically fluorocarbon-in-water emulsions having a discontinuous fluorocarbon phase and a continuous aqueous phase. The emulsions typically include emulsifying agents and osmotic agents, together with buffers and electrolytes.

The fluorocarbon emulsion may be selected from a wide range of suitable emulsions. Advantageously, it is a fluorocarbon-in-water emulsion, having a preferred fluorocarbon concentration of about 5% to about 125%, w/v.

Fluorocarbons are fluorine substituted hydrocarbons that have been used in medical applications as imaging agents and as blood substitutes. U.S. Pat. No. 3,975,512 to Long uses fluorocarbons, including brominated perfluorocarbons, as a contrast enhancement medium in radiological imaging. Brominated fluorocarbons and other fluorocarbons are known to be safe, biocompatible substances when appropriately used in medical applications.

It is additionally known that oxygen, and gases in general, are highly soluble in some fluorocarbons. This characteristic has permitted investigators to develop emulsified fluorocarbons as blood substitutes. For a general discussion of the objectives of fluorocarbons as blood substitutes and a review of the efforts and problems in achieving these objectives see "Reassessment of Criteria for the Selection of Perfluorochemicals for Second-Generation Blood Substitutes: Analysis of Structure/Property Relationship" by Jean G. Riess, *Artificial Organs* 8:34–56, 1984.

The fluorocarbon, in one preferred embodiment, is a perfluorocarbon or substituted perfluorocarbon. Fluorocarbon molecules used in these emulsions may have various structures, including straight or branched chain or cyclic structures, as described in Riess, J., Artificial Organs 8(1):44–56 (1984). These molecules may also have some degree of unsaturation, and may also contain bromine or hydrogen atoms, or they may be amine derivatives. The fluorocarbons may be present in the emulsion in any useful concentration, but usually range from about 5% to 125% weight per volume (w/v). As used throughout, concentrations defined as weight/volume are understood to represent grams/ml and % weight per volume to represent grams/100 ml.

Although concentrations as low as 5%, w/v are contemplated, in a preferred embodiment the concentrations are at least 25% or 30%, preferably at least 40%, 50%, 55%, 60%, 75% or 80% w/v. Emulsions of 85%, 90%, and 100% are particularly preferred. Preferred fluorocarbon emulsion formulations are those disclosed in U.S. Pat. Nos. 4,865,836; 4,987,154; and 4,927,623, which are hereby incorporated by reference.

There are a number of fluorocarbons that are contemplated for use in the present invention. These fluorocarbons include bis (F-alkyl) ethanes such as $C_4F_9CH=CH_4CF_9$ (sometimes designated "F-44E"), i-$C_3F_9CH=CHC_6F_{13}$ ("F-i36E"), and $C_6F_{13}CH=CHC_6F_{13}$ ("F-66E");cyclic fluorocarbons, such as C10F18 ("F-decalin", "perfluorodecalin" or "FDC"), F-adamantane ("FA"), F-methyladamantane ("FMA"), F-1,3-dimethyladamantane ("FDMA"), F-di-or Ftrimethylbicyclo[3,3,1]nonane ("nonane"); perfluorinated amines, such as F-tripropylamine ("FTPA") and F-tri-butylamine ("FTBA"), F-4-methyloctahydroquinolizine ("FMOQ"), F-n-methyl-decahydroisoquinoline ("FMIQ"), F-n-methyldecahydroquinoline ("FHQ"), F-n-cyclohexylpurrolidine ("FCHP") and F-2 -butyltetrahydrofuran ("FC-75" or "RM101").

Other suitable fluorocarbons may be selected from brominated perfluorocarbons, such as 1-bromo-heptadecafluorooctane ($C_8F_{17}Br$, sometimes designated perfluorooctylbromide or "PFOB", now known by the U.S. Adopted Name "perflubron"), 1-bromopentadecafluoroheptane ($C_7F_{15}Br$), and 1-bromotridecafluorohexane ($C_6F_{13}Br$, sometimes known as perfluorohexylbromide or "PFHB"). Other brominated fluorocarbons are disclosed in U.S. Pat. No. 3,975,512 to Long. Also contemplated are fluorocarbons having nonfluorine substituents, such as perfluorooctyl chloride, perfluorooctyl hydride, and similar compounds having different numbers of carbon atoms, e.g., 6–12 carbon atoms.

Additional fluorocarbons contemplated in accordance with this invention include perfluoroalkylated ethers or polyethers, such as $(CF_3)_2CFO(CF_2CF_2)_2OCF(CF_3)_2$, $(CF_3)_2CFO-(CF_2CF_2)_3OCF(CF_3)$, $(CF_3)CFO(CF_2CF_2)F$, $(CF_3)_2CFO(CF_2CF_2)_2F$, $(C_6F_{13})_2O$. Further, fluorocarbon-hydrocarbon compounds, such as, for example compounds having the general formula $C_nF_{2n+1}$-$C_{n'}F_{2n'+1}$, $C_nF_{2n+1}OC_{n'}F_{2n'+1}$, or $C_nF_{2n+1}CF=CHC_{n'}F_{2n'+1}$, where n and n' are the same or different and are from about 1 to about 10 (so long as the compound is a liquid at room temperature). Such compounds, for example, include $C_8F_{17}C_2H_5$ and $C_6F_{13}CH=CHC_6H_{13}$. It will be appreciated that esters, thioethers, and other variously modified mixed fluorocarbon-hydrocarbon compounds are also encompassed within the broad definition of "fluorocarbon" materials suitable for use in the present invention. Mixtures of fluorocarbons are also contemplated. Additional "fluorocarbons" not listed here, but having those properties described in this disclosure that would lend themselves to use in vivo in accordance with the present invention are also contemplated.

Emulsifying agents used in the emulsions of this invention may be anionic, cationic or non-ionic surfactants or combinations thereof as are well known to those in the chemical arts or they may be mixtures of synthetic compounds such as Pluronic F-68, a condensate of ethylene oxide with propylene glycol, as used in U.S. Pat. No. 4,073,879 to Long. Fluorosurfactants, such as those described by J. Riess et al. Int'l Symposium on Blood Substitutes, Montreal, May, 1987, are particularly suitable can also be used. Emulsifying agents may also be mixtures of the above agents. Particularly suitable emulsifiers may include natural amphipathic compounds such as phospholipids, particularly phosphatidylcholine, wherein combined hydrophilic and hydrophobic properties enable the molecule to interface with both aqueous and fluorocarbon systems, thereby forming the emulsion droplets. There are various species of each class of phospholipids, such as the phospholipid cholines, comprising various pairings of saturated and unsaturated fatty acids in the glycerol structures. Phosphatidylcholine is an abundant natural material (lecithin) which may be purified from egg yolk, or may be produced synthetically (Avanti Polar Lipids, Pelham, Ala.). Phospholipid emulsifiers, particularly egg yolk phospholipid and lecithin, are particularly preferred.

The phospholipid emulsifying agent should be included in the range of from 2 to 14% w/v, usually increasing the phospholipid concentration with increasing fluorocarbon concentration. The preferred amount for an emulsion comprising 75% w/v bromofluorocarbon is 2.5 to 5% w/v and 3.5 to 10% w/v of phospholipid for an emulsion with 100% w/v bromofluorocarbon. In a preferred embodiment, the phospholipid comprises at least 2 % w/v of the emulsion.

Emulsification requires large amounts of energy to convert a two-phase immiscible system into a suspension of discontinuous small droplets of hydrophobic fluid in an aqueous continuous phase. Fluorocarbon emulsification may be carried out generally by either of two general processes which provide energy to the system to break up the fluorocarbon volume into small droplets. In sonication emulsification, a probe is inserted into the mixture of fluorocarbon, emulsifier, and aqueous phase, and bursts of energy are released from the tip of the probe. In a mechanical emulsification process, such as that performed by a Microfluidizer TM apparatus (Microfluidics, Newton, Mass. 02164), streams of the mixed emulsion components are directed through the apparatus at high velocity and under high pressure (e.g. 15,000 psi), and the high shear forces or cavitation resulting from the mechanical stress applied to the fluid produce the emulsion.

The aqueous phase of the emulsion may have components dissolved therein which give the emulsion desirable properties. For example, it may comprise an osmotic agent to bring the emulsion to physiological isotonicity. The osmotic agent may be sodium chloride, or it may be a polyhydroxyl compound, such as a sugar or mannitol. The aqueous phase will also contain soluble buffering agents.

The lipid phase of the emulsion may also have components dissolved therein. For example, a phosphatidyl choline emulsifier may have glycerol, phosphatidyl glycerol, other phospholipids or cholesterol admixed, and further contain an antioxidant substance, such as a tocopherol, to protect against lipid oxidation.

Several fluorocarbon emulsions have been produced commercially for use as intravascular oxygen carriers. These include a mixed decalin emulsion sold by Alpha Therapeutics Corp. under the trademark FLUOSOL and perflubron emulsions produced by Alliance Pharmaceutical Corp. of San Diego, Calif.

One exemplary perflubron emulsion is a 90% (w/v) perflubron emulsion referred to as Oxygent TM HT having the following Formula I:

| FORMULA I PERFLUBRON EMULSION | |
| --- | --- |
| Component | Percent (w/v) |
| Perflubron | 90.000 |
| Egg Yolk Phospholipid | 4.000 |
| NaH$_2$PO$_4$.H$_2$O, USP | 0.052 |
| Na$_2$HPO$_4$.7H$_2$O, USP | 0.355 |
| NaCl, USP | 0.280 |
| EDTA, USP | 0.020 |
| d-α-tocopherol, USP | 0.002 |
| Water for injection, | 48.400 |

Hemoglobin compositions contemplated for use in the present invention are well known. Such compositions are disclosed, for example, in the following U.S. Patents, which are hereby incorporated by reference: U.S. Pat. Nos. 4,911,929; 4,861,867; 4,857,636; 4,777,244; 4,698,387; 4,600,531; 4,526,715; 4,473,494; and 4,301,144.

Various materials have been used successfully as plasma expanders in connection with hemodilution procedures. These include the well-known categories of crystalloid compositions (exemplified by Ringers-lactate and saline (0.9%) both from Baxter Healthcare Corp., Deerfield, Ill.) and colloid compositions. Colloid compositions include (1) modified fluid gelatins, such as those sold under the following trademarks: Plasmagel ® (R. Bellon Lab., Neuilly-sur Seine, France), Gelifundol ® (Biotest, Frankfurt, Germany), Haemacel ® (Hoechst-Roussel Pharmaceutical Inc., Sommerville, N.J.); (2) dextran solutions, such as those sold under the trademarks Macrodex ® (dextran-70) and Rheomacrodex ® (dextran-40) both from Pharmacia, Piscataway, N.J.); (3) albumin solutions, such as those sold under the trademark Albutein ® (Alpha Therapeutics, Los Angeles, Calif.) and human serum albumin (5%) from Abbott Labs, North Chicago, Ill.; (4) starch solutions such as Hetastarch (Hycroxyethylstarch) Hespan ® (DuPont, Willmington, Del.). These are administered in various volumes to maintain the patient's blood volume in the normal range and to encourage the increase in cardiac output that accompanies hemodilution procedures. In general, crystalloid-based solutions need to be given in volume ratios of 2:1 or 3:1 to blood withdrawn; colloids are usually given in lesser amounts.

C. Procedures

Autologous blood use virtually eliminates the possibility of contracting blood-borne diseases associated with transfusions. Autologous blood for use in subsequent transfusions can be obtained in a number of ways, including one or more of the following: predeposit; perioperative isovolemic hemodilution; intraoperative salvage; and postoperative salvage.

Predeposit requires that the surgery be planned well in advance of the actual date. Blood is donated by the patient during the weeks and months before surgery, and is stored for subsequent administration to the patient. Phlebotomies of 350–400 ml are typically performed at 2-7 day intervals, with the last collection more than 72 hours before surgery. The blood may be stored in the liquid state as whole blood, or it may be divided into red cells and plasma which can be frozen to preserve labile components.

Perioperative isovolemic hemodilution is the process of collecting blood immediately before a surgical procedure with the concomitant replacement by a sufficient volume of crystalloid or colloid solution. This practice decreases blood viscosity during surgery, thereby reducing the work load on the heart and increasing microcirculation. Typically, sufficient blood is removed to reduce the hematocrit from a typical normal value of approximately 0.45 to about 0.20 to 0.35, preferably about 0.25 to about 0.30. This blood is stored for readministration to the patient during or after surgery. After removal of some of the blood, or simultaneously with the removal, a crystalloid or colloid plasma expander (or both) is administered to the patient to maintain blood volume at a desired value, typically at the normal value.

Intraoperative blood salvage involves collecting blood lost from a wound or body cavity during surgery, processing it, and reinfusing the processed blood into the same patient. This procedure is safe and effective if certain basic precautions are followed to ensure against contamination of the blood with bacteria or other pathogens, or malignant cells. Autotransfusion devices for collecting, filtering, and reinfusing the blood are commercially available. Also, some devices separate and wash the red blood cells, thereby avoiding administration of blood contaminated by debris, irrigating solutions, activated factors, anticoagulants, and free hemoglobin. Suitable devices of this type are exemplified by the Haemonetics Cell Separation and Cell Washer, Haemonetics Corp., Braintree, Mass.

Postoperative salvage and autotransfusion involves the recovery of blood drained from the surgical wound during the hours following the operation. If basic precautions are taken to insure the sterility of the collected blood, the procedure is safe and well tolerated. The same commercial devices can be used for this procedure as for intraoperative blood salvage.

Detailed reviews of autologous blood procedures and acute isovolemic or normovolemic hemodilution are found, for example, in Stehling, et al., Transfusion 31:857 (1991) and Mercuriali, et al, Autologous Blood, Transmedica Europe Limited, Eastbourne, United Kingdom (1991), which are hereby incorporated by reference.

In the practice of the present invention, autologous blood procedures (preferably involving perioperative hemodilution) are combined with administration of non-blood oxygen carriers, including hemoglobin compositions and, more preferably, fluorocarbon emulsions. The invention below combines the use of dose-limited and short intravascular half-life oxygen carrying drugs with autologous blood transfusion techniques, including in particular, predonation and perioperative hemodilution techniques. In patients who have donated blood prior to surgery (predonation) an oxygen-carrying drug can be infused during surgery to support adequate oxygen delivery, thereby conserving the autologous blood for definitive correction of anemia at the end of surgery or post operatively. Small amounts of the oxygen carrying drug (less that 50% of blood volume), are effective in providing this margin of safety during the surgery period when cardiac output elevation occur due to lower blood viscosity. This method further reduces or eliminates the need for administering homologous blood to the patient.

Similarly, a dose-limited oxygen-carrying drug with short intravascular persistence which does not cause adverse hemodynamic effects, can be used effectively as an additive to standard perioperative hemodilution. As outlined above, the oxygen supplementation provided by the drug would provide a margin of safety during the actual surgery. In this clinical setting, the additional margin of safety is afforded to the hemodiluted patient, by augmenting total oxygen delivery during surgery and conserving autologous blood for the definitive correction of anemia at the end of surgery or post operatively. The need for homologous blood is thereby reduced or eliminated.

In particular, one embodiment of the invention involves removal of a portion of the patient's blood, and administration of an intravenous fluid to reduce the hematocrit from about 0.45 to between 0.20 to about 0.35, preferably from about 0.25 to about 0.30. This removal is usually deliberate, although the invention may also be used with trauma victims or other patients suffering involuntary blood loss. With deliberate removal, the blood is stored for readministration to the patient at a later time.

Either simultaneously with or after removal of the blood, sufficient intravenous fluid is administered to permit regulation of cardiac output in order to maintain oxygen delivery at a level at least approximately equivalent to levels prior to removal of the patient's blood, in a manner well known in the hemodilution art. This intravenous fluid includes an oxygen carrier other than red blood cells, preferably a biocompatible fluorocarbon emulsion of the type previously discussed, although hemoglobin compositions are also contemplated, as are other oxygen carriers. In addition, the intravenous fluid preferably includes a plasma expander, such as a colloid or crystalloid.

Advantageously, the volume of intravenous fluid administered to the patient is at least about equal to 75%, preferably at least about 100% of the volume of blood removed from the patient. More preferably, the volume of intravenous fluid is between about 150% and 300% of the volume of blood removed, depending on whether the fluid is predominantly a colloid or a crystalloid. Alternatively, the volume of intravenous fluid administered to the patient is adequate to reduce the hematocrit of the patient to the levels discussed above.

In one embodiment of the invention, the intravenous fluid comprises a major portion of a plasma expander and a minor portion of oxygen carrier. The volume ratio of administered expander to an oxygen carrier will range from 1:1 to at least 10:1, depending on whether the fluid is a crystalloid or a colloid, and on the composition of the oxygen carrier, the concentration of the oxygen carrier, $PO_2$ and cardiac output. These ranges are most desirable when using a high concentration fluorocarbon emulsion, having at least about 40%, preferably at least about 50% or 60% fluorocarbon, w/v.

In one preferred embodiment, where a fluorocarbon emulsion such as perflubron emulsion is used as the oxygen carrier, the amount of actual perfluorocarbon administered to the patient is advantageously from about 0.5 g/kg to about 10 g/kg, preferably 2-6 g/kg, based on the weight of the patient. When a 90% w/v or 100% w/v fluorocarbon emulsion is used, the volume of emulsion necessary to deliver the desired dosage is about 0.5 or 0.55 ml/kg to about 10 or 11 ml/kg, preferably about 2 to 6 ml/kg. Simple calculation provides the preferred volume of emulsion when different concentrations of fluorocarbon are used.

The hemodiluted patient is then administered a breathing gas enriched in oxygen, preferably at least 50-60%, and most preferably 100% oxygen. The effects of the enriched breathing gas, increased cardiac output due to hemodilution, the oxygen carrier, and the dissolved oxygen in the aqueous portion of the circulating intravascular fluid all combine to supply enhanced levels of oxygen to the patient. The collective contributions of these factors to oxygen delivery in the patient are discussed in more detail in sections D. and E. below.

During or after the surgical procedure (or other condition resulting in blood loss), the autologous blood removed from the patient (or the red cell portion thereof) can be readministered to the patient. The oxygen carrier, meanwhile, is cleared from the circulation in a relatively short time, and its oxygen-carrying function is supplanted by the autologous transfusion of red cells, if required.

D. Oxygen Delivery to Tissues

Although not intending to be bound to any particular theory of operation, the following discussion provides a framework for understanding the physical and physiological mechanisms contributing to the function of the present invention.

Oxygen transport to tissues can be considered to occur via two processes. The first, is the convective (bulk) delivery of $O_2$ to tissues, and the second is the delivery of $O_2$ to tissues via a diffusive process.

(1) Convective Oxygen Delivery

The first process, convective $O_2$ delivery, is described by the Fick equation shown below, where $VO_2$.

=oxygen consumption, C.O.=cardiac output, and (a−v)O$_2$=the arterial-venous O$_2$ content difference.

$$VO_2 = [(C.O.)] \times [(a-v)O_2]$$

Although the Fick equation is quite straightforward, a number of physiological variables of importance are imbedded in it. For example, the arterial-venous differential in oxygen content [(a−v)O$_2$] is determined by the O$_2$ content of both arterial (CaO$_2$) and venous (CvO$_2$) blood, respectively, which, in turn, is directly related to the hemoglobin (Hb) concentration and the O$_2$ saturation. Oxygen saturation is determined by the PO$_2$ and by the position of the oxyHb (oxygenated form of Hb) dissociation curve. The PO$_2$ is determined by the O$_2$ tension in the inspired air and the capacity of the lung to oxygenate pulmonary capillary blood. Finally, the position of the oxyHb dissociation curve is determined by 2,3-diphosphoglycerate (2,3-DPG) as well as pH and pCO$_2$, which differ between arterial and venous blood.

Similarly, cardiac output (C.O.) is controlled by many factors, including heart rate, the left ventricular filling volume (i.e., stroke volume), and the demand for O$_2$ in tissues (i.e., oxygen consumption, VO$_2$). Assuming a constant blood volume and under stable hemodynamic conditions, the left ventricular filling volume is proportional to the blood viscosity, which, in normal humans, is primarily a function of the hematocrit (percent of red cells in blood).

Some of these complex relationships can be shown graphically (see FIG. 1). In FIG. 1, O$_2$ content is plotted against O$_2$ tension, PO$_2$. FIG. 1 presents data for a normal, 70 kg man at rest with a hemoglobin concentration of 14.4 g/dl (hematocrit=45%). The data for the oxyHb dissociation curve used to create this graphic representation were generated by the model developed by Winslow (1985), which calculates the total O$_2$ contents dissolved in the plasma and bound to hemoglobin. For a given arterial and venous PO$_2$ of 100 and 40 torr, respectively, the arterial to venous oxygen content difference (CaO$_2$−CvO$_2$) is 5 mL/dL. At a normal cardiac output of 5 L/min, the O$_2$ consumption (VO$_2$, represented by the cross-hatched area) is approximately 250 mL/min or 5 mL/kg/min.

Normally, more O$_2$ is delivered to tissue than is utilized, providing a "margin of safety." When the convective (bulk) delivery of O$_2$ decreases below a certain critical point, tissue function may be compromised, with various consequences such as tissue hypoxia, production of lactic acid, infarction, necrosis, etc. Once this critical oxygen delivery level is reached (i.e., when O$_2$ delivery is severely limited), then VO$_2$ (oxygen consumption) will be supply-limited. The actual value for the critical oxygen delivery level is very difficult to specify, since there are likely to be different values for different organs or different capillary beds.

When O$_2$ consumption is not supply-limited, changes in O$_2$ content of the arterial blood can be compensated for by other normal physiological mechanisms. For example, in anemia, the cardiac output becomes elevated (see below), as does the level of red cell 2,3-DPG. The latter serves to shift the oxyHb dissociation curve to the right (reduced affinity, increased P$_{50}$ [the PO$_2$ at which hemoglobin is 50% saturated with O$_2$]).

A similar compensatory mechanism (with respect to the cardiac output) occurs during acute normovolemic hemodilution (Messmer et al. Res. Exp. Med. 159:152-56 (1986)). As the hematocrit decreases during the hemodilution, blood viscosity also decreases significantly, which allows the cardiac output to increase without any significant changes in the work load on the heart. In this way, total oxygen consumption can be maintained. This is illustrated in FIG. 1, where it can be seen that the amount of oxygen consumption from hemoglobin (i.e., total area of lighter shading) is the same in both FIG. 1 (before hemodilution) and FIG. 2 (after hemodilution).

Work by Guyton et al. Cardiac Output and its Regulation, 2nd Ed. Saunders, Philadelphia (1973)) has shown that over a broad range, the cardiac output varies inversely with hematocrit, with an "optimum hematocrit" in approximately the range of 40 to 45% for normal, resting humans. When hematocrit values exceed 45%, blood viscosity limits cardiac output such that there is little beneficial effect from the additional O$_2$ carrying capacity of the increased number of circulating red cells. When the hematocrit is less than about 40%, the lower viscosity results in a decreased total peripheral resistance to blood flow which allows cardiac output to increase in order to maintain normal oxygen delivery.

It should be noted that augmenting O$_2$ transport by administration of a cell-free oxygen carrier differs from simple transfusion in several important ways. A key point in understanding the value of a low-dose acellular "blood substitute" is that plasma O$_2$ is increased, rather than red cell O$_2$, as is the case with transfusion of blood. Transfusion of red cells will increase bulk blood viscosity, which can cause a decrease in cardiac output and therefore may not increase the bulk O$_2$ delivery.

Figure 2:
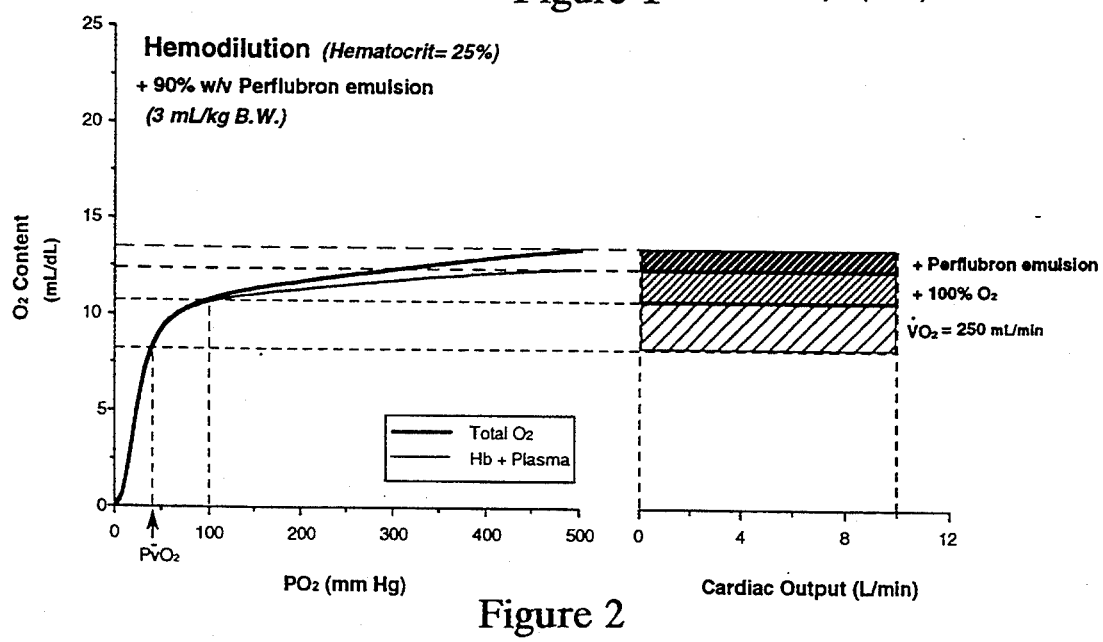
FIG. 2 is a graph showing oxygen delivery and total $O_2$ consumption following acute normovolemic hemodilution (to a hematocrit of 25%) and injection of 3.0 mL/kg BW of a 90% w/v perflubron emulsion (Oxygent HT) while breathing 100% $O_2$. The potential contributions to total $O_2$ consumption ($VO_2$) by the individual compartments (i.e., the red cells, plasma, and the perflubron emulsion) is shown by the different cross-hatched areas. At a cardiac output of 10 L/min, (and an arterial $pO_2$ of 500 mmHg) the total amount contributed to $VO_2$ by the plasma and perflubron phase alone approximately equals normal $VO_2$.

Addition of a cell-free O$_2$ carrier, on the other hand, will increase bulk O$_2$ delivery by elevating the O$_2$ content of the plasma and potentially increasing the cardiac output (since overall blood viscosity would be reduced). FIG. 2 illustrates the increase in potential oxygen consumption which can be achieved by elevating the O$_2$ content of blood by breathing 100% O$_2$.

This additional contribution to VO$_2$ is primarily due to an increased amount of O$_2$ dissolved in the plasma compartment. Theoretically, VO$_2$ can be further increased by addition of a low dose of a 90% w/v perflubron emulsion under these conditions which would provide an even greater margin of safety. FIG. 2 illustrates the additional increase in potential oxygen consumption which can be achieved with a overall dose of a 90% w/v perflubron emulsion.

(2) Diffusion Oxygen Delivery

Oxygen transport to tissue also occurs via diffusion. There are a series of diffusion boundaries through which O$_2$ must pass on its way from the red cell to the tissues. Fick's law of diffusion states that the overall rate of diffusion of a gas from one compartment to another is governed by the diffusion gradient, the difference between the gas concentrations (P$_1$−P$_2$) within the two compartments, and a diffusion constant, K$_d$, which is a lumped-sum reflection of many factors including properties of the boundary layers, temperature, etc.

$$\frac{d(O_2)}{dt} = K_d(P_c - P_t)$$

The process of O$_2$ diffusion can be simply illustrated by considering the movement of water through holes in a wall separating a higher elevation reservoir and a lower level reservoir. Water is supplied initially at one elevation (P$_1$), and flows to a second lower level (P$_2$).

The hydrostatic pressure driving this movement is the vertical difference in height between the two reservoirs. The total rate of water movement is also limited by the cross-sectional area of the holes in the barrier which provide resistance to flow from compartment 1 to 2. In this analogy, the two water levels correspond to the two $O_2$ pressures ($P_1$ and $P_2$) in Ficks law of diffusion, shown above, and the cross-sectional area of the holes in the barrier (through which the water flows) would be represented by the diffusion constant, $K_d$.

Experimental work has shown that there are probably two barriers to diffusion of $O_2$ from the red cell to the tissues: the layer of unstirred plasma surrounding the red blood cell, and the collective membranes separating the plasma space from the cellular cytosol of adjacent tissue. Raising the level of $O_2$ in the plasma will have the effect of increasing the rate of diffusion into tissues, since the plasma represents an "intermediate level reservoir" in the preceding analogy. In fact, if there is not a limiting supply of $O_2$ in red cells, then the rate of movement of $O_2$ from plasma to tissues will be proportional to this plasma reservoir. This represents the essence of the proposed use of low-dose $O_2$ carriers to reduce the need to transfuse homologous blood.

The proposed mechanism assumes that a small reduction of the reservoir of available $O_2$ (e.g., hemodilution) will not appreciably change the overall rate of diffusion because it is assumed that the barrier to diffusion represented by the membranes between the plasma and tissue cytosol space is rate-limiting. Experimental evidence exists to support this assumption.

Increasing the diffusive delivery of $O_2$ to tissue is sometimes called "diffusion facilitation", and could increase $O_2$ delivery to tissues under conditions where $O_2$ delivery might be otherwise supply-limited. In other words, increasing the dissolved (plasma) $O_2$ concentration is expected to decrease the level at which critical $O_2$ delivery occurs and thereby increase the margin of safety in terms of prevention of tissue hypoxia. Experimental evidence suggests that this is, in fact, the case. In a recent study by Faithfull & Cain J. Crit. Care 3:14–18 (1988)), dogs were initially hemodiluted with either 6% dextran (average molecular weight 70,000, in Tyrodes solution), or the perfluorocarbon emulsion, Fluosol, and then progressively hemorrhaged to determine the critical $O_2$ extraction ratios. Fluosol-treated dogs had lower mixed venous $PO_2$ levels and higher $O_2$ extraction fractions at the critical $O_2$ delivery point. This indicated that perfluorochemicals in Fluosol may have promoted diffusion of $O_2$ into the tissues. This effect was very evident in these Fluosol studies since these dogs likely had a compromised microcirculation due to the severe capillary flow inhomogeneity that occurs in dogs immediately following injection of only 1 to 2 mL of the Fluosol emulsion (Faithfull et al. Microvase. Res. 33:183–93 (1987)).

It should be noted that transfusion of red cells will not affect $O_2$ diffusion in the same manner as described. In fact, an additional physiological effect described by Federspiel et al. Microvasc. Res. 32:164–89 (1986)), refers to the fact that in normal capillary beds, red cells are separated by considerable distances as they individually traverse the capillary network. The $O_2$ would be expected to transfer from red cells to tissue predominantly across the area where the red cell is closely in contact with the endothelial cells lining the vasculature. Addition of a cell-free $O_2$ carrier might increase the rate of $O_2$ transfer, simply on the basis that more $O_2$ would be in contact with the endothelial cells.

In general, improvement of blood fluidity by hemodilution has been shown to increase mean tissue $PO_2$ in various organs (Messmer et al. Res. Exp. Med. 159:152 –56 (1973)). This increase in tissue $PO_2$ was attributed to more even flow distribution at the microcirculatory level and was interpreted as improved tissue oxygenation. On the other hand, Homer Microvasc. Res. 22:308–23 (1981)) argued that in acute anemia there may be large differences between red blood cell $PO_2$ and the plasma $PO_2$. This would occur as a result of $O_2$ diffusion from the red cell being slowed by passage through the plasma (which has very low $O_2$ solubility characteristics). With hemodilution, the spacing between red blood cells in tissue capillaries is increased so that outward diffusion of $O_2$ from red cells is slowed further by the increased diffusional barrier of plasma. The resultant gradient for $PO_2$ may not be resolved (i.e., not all the oxygen has time to unload) during the short time that the red cell dwells in the capillary and $O_2$ extraction may be diminished accordingly (Gutierrez, Respirat. Physiol. 63:79–96 (1985)).

The presence of an additional $O_2$ carrier such as a perfluorochemical in the plasma will increase the total $O_2$ content in the plasma compartment of blood and may facilitate the diffusion of $O_2$ from the red cell into the tissues. According to the model (see FIG. 2), the addition of a relatively small dose (3 mL [2.7 g perflubron]/kg BW) of a highly concentrated 90% w/v perflubron emulsion will result in a significant increase in the total $O_2$ content in the plasma. When performed during respiration with 100% $O_2$ and in the presence of acute normovolemic hemodilution (to a hematocrit of 25%), the net result would represent a doubling of the oxygen consumption. Normal oxygen consumption would come preferentially from the perflubron and the plasma, since this $O_2$ is physically dissolved and therefore readily available (compared to the $O_2$ that is chemically bound to hemoglobin as a ligand). The remaining $O_2$ carried by the red cells would therefore represent an available reservoir of extra $O_2$ that would supply additional oxygen, when needed, to prevent certain sensitive tissues from reaching a critical level of $O_2$ delivery.

In summary, a low-dose cell-free oxygen carrier is superior, in terms of tissue oxygenation, to additional red cell transfusion. Such an oxygen carrier is used for the temporary enhancement of oxygen delivery during the acute phase of surgery. None of the currently available oxygen carriers can be considered effective "blood substitutes" because of their short retention time in the circulation (hours) compared to red cells (months). With routine use, especially in uncomplicated elective surgery combined with acute normovolemic hemodilution procedures, the need for transfusion (i.e., "transfusion trigger") can be reduced. This can eliminate the need for transfusion of homologous red blood cells in many cases and, thereby, significantly reduce the risk of transfusion-borne disease.

E. EXAMPLES

EXAMPLE 1

Enhancement of $O_2$ Delivery By Perfluorocarbon Emulsion Following Acute Hemodilution in Dogs This example was designed to determine the efficacy of oxygen delivery by 90% w/v perflubron emulsion formulation to Formula I in anesthetized mongrel dogs (n=9) subjected to acute normovolemic hemodilution. Four control animals (injected with 3.3 mL Ringer's-lactate/kg body weight) were included in this study. A bolus injection of epinephrine was used in all dogs to contract the spleen and release sequestered red blood cells prior to hemodilution. Following this injection, and prior to beginning the hemodilution process, baseline measurements were obtained for cardiac output, mean arterial pressure, heart rate, pulmonary artery pressure, pulmonary wedge pressure, arterial and venous blood gases, hematocrit, and total blood oxygen content. During hemodilution (breathing room air) to a hematocrit of approximately 25%, each aliquot of blood removed was immediately replaced with 3 volumes of Ringers-lactate (R-L). Following this, blood samples were collected for measurement of all variables. Dogs were then ventilated with 100% oxygen and further hemodiluted to a hematocrit of approximately 10–12%. During this second hemodiluted procedure, the blood volume removed was replaced with 1–1.5 volumes of colloid, consisting of the dog's plasma (collected during the first hemodilution) and supplemented with an albumin solution (5% HSA in R-L). Following this, blood samples were again drawn for measurement of all variables. A 90% w/v perflubron emulsion having the composition of Formula I was injected to a total dose of 3.3 mL [3.0 g perflubron]/kg body weight at a rate of approximately 20–30 mL/min, and blood samples were drawn at various intervals for a total of 3 hours.

Figure 3:
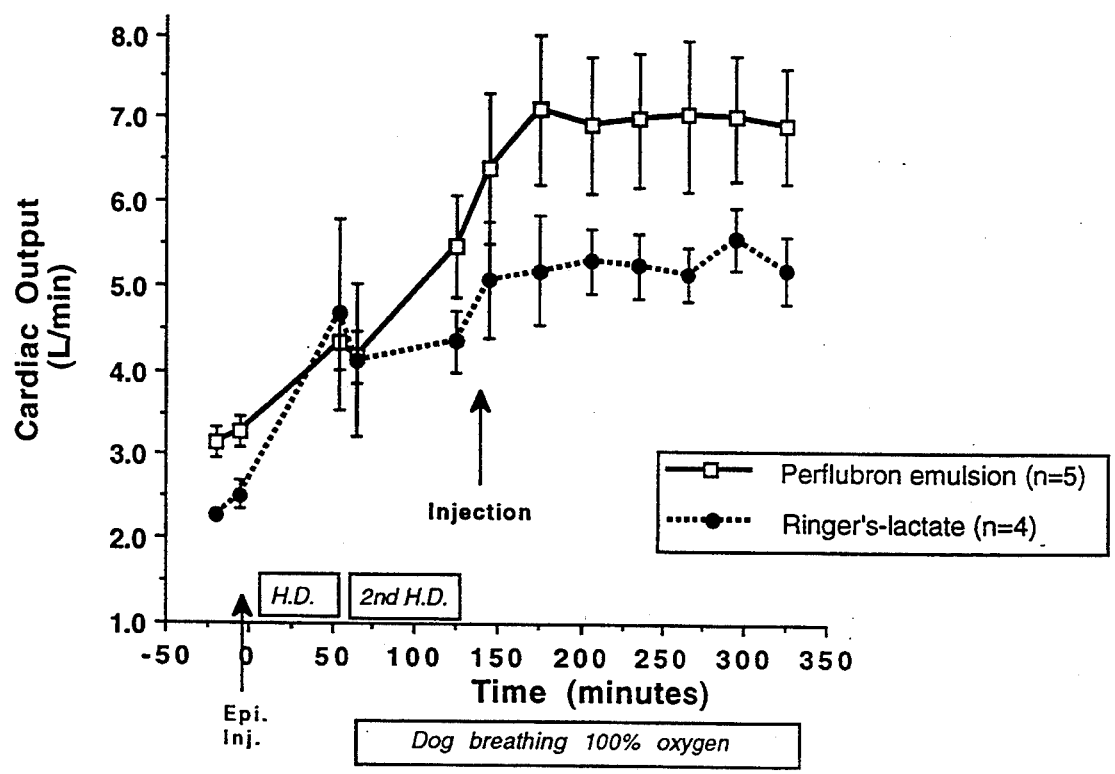
FIG. 3 is a graph showing the cardiac output in anesthetized dogs during and following acute crystalloid hemodilution. Data are Means±SEM.
Figure 4:
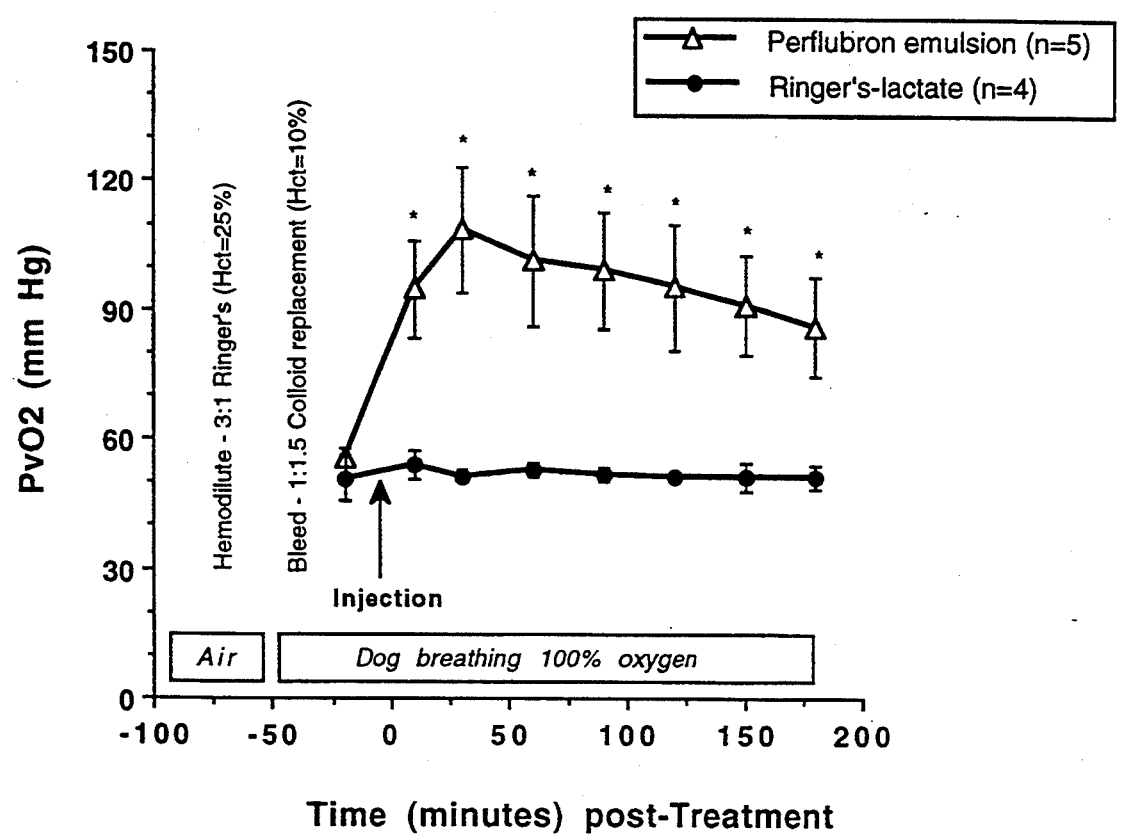
FIG. 4 is a graph showing mixed venous $PO_2$ in anesthetized dogs during and following severe crystalloid hemodilution. * Indicates a significant difference between the two groups. Data are Means±SEM.

As expected, cardiac output rose significantly following hemodilution, primarily because of the reduction in blood viscosity at the lower hematocrits (FIG. 3), and was able to reach even higher levels in the perflubron emulsion-treated dogs. Mixed venous $PO_2$ was significantly higher following infusion of the 90% w/v perflubron emulsions compared to controls at all timepoints during the 3 hour post-injection monitoring period (FIG. 4).

Figure 5:
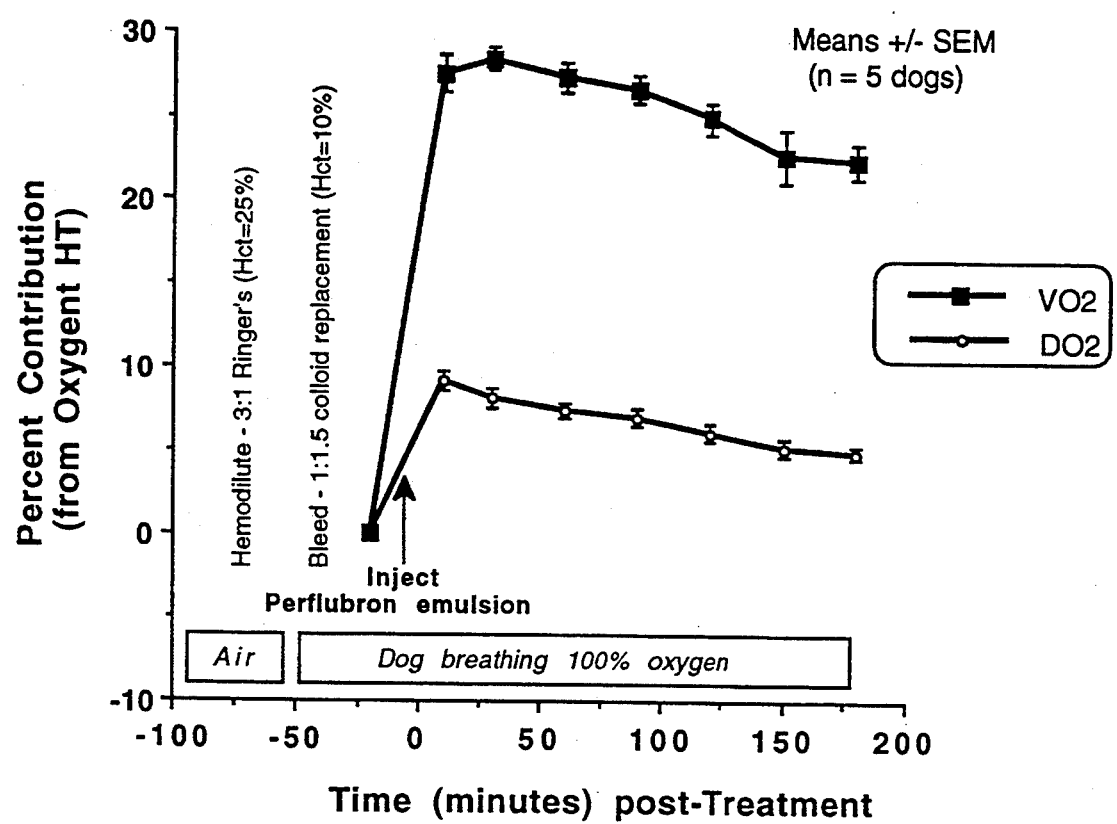
FIG. 5 is a graph showing the percent of oxygen delivery and total oxygen consumption contributed only by the $O_2$ dissolved in the perflubron emulsion in anesthetized dogs following severe crystalloid hemodilution. * Indicates a significant difference between the two groups. Data are Means±SEM.
Figure 6:
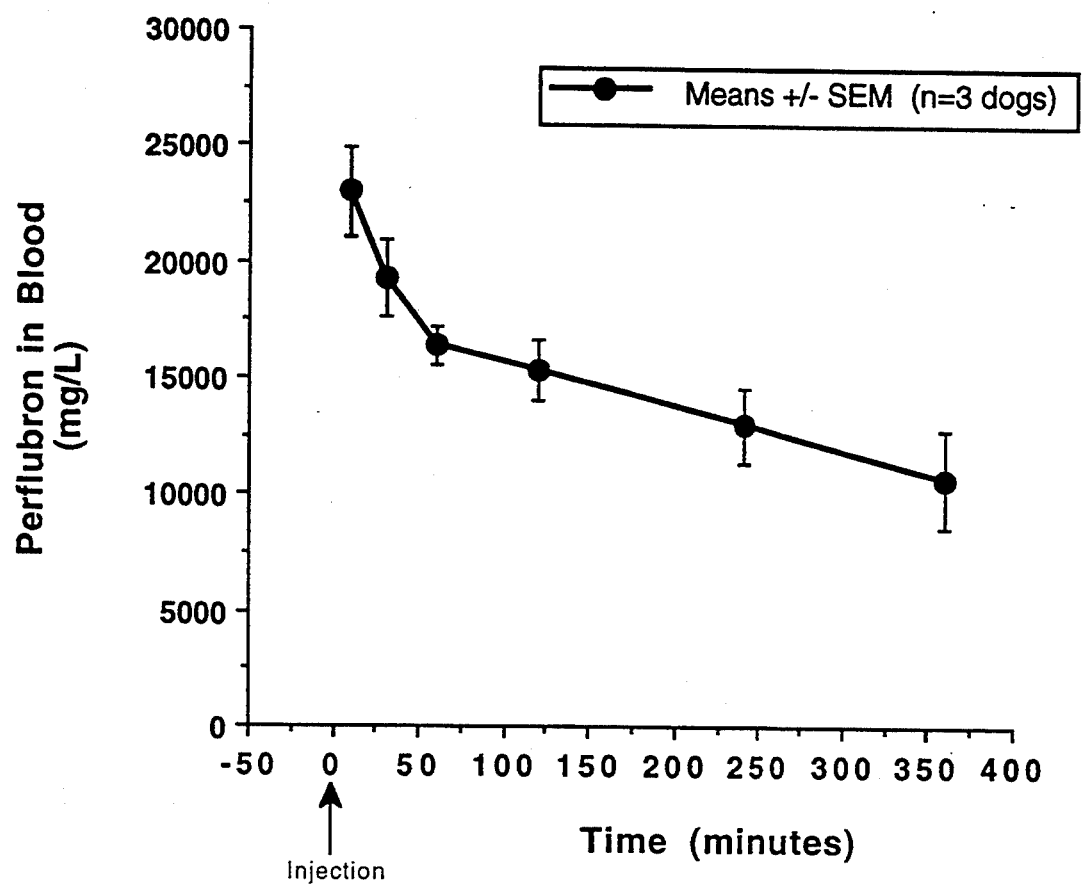
FIG. 6 is a graph showing perflubron levels in the blood as a function of time following injection of perflubron emulsion.
Figure 7:
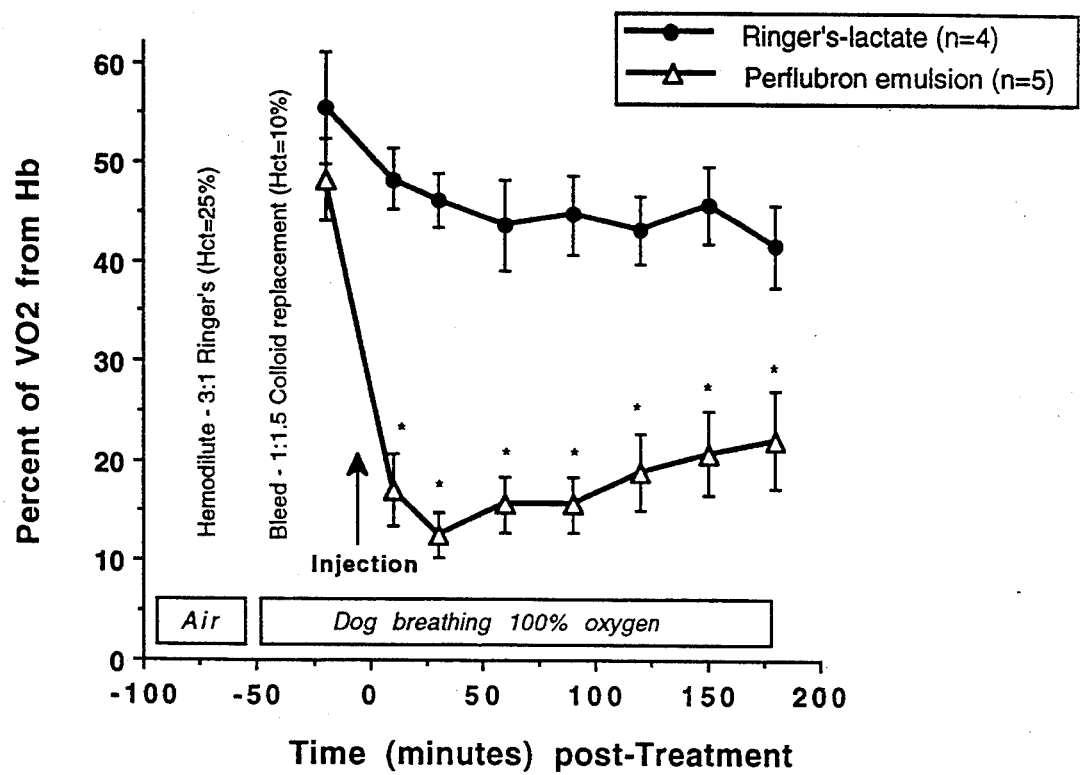
FIG. 7 is a graph showing the percent of total oxygen consumption contributed only by the $O_2$ bound to hemoglobin in anesthetized dogs following severe crystalloid hemodilution. * Indicates a significant difference between two groups. Data are Means±SEM.

The percent of total oxygen delivery ($DO_2$) contributed by the perflubron emulsion-dissolved $O_2$ was approximately 8% to 10%, while total oxygen consumption ($VO_2$) contributed by the perflubron emulsion-dissolved $O_2$ was approximately 25–30% (FIG. 5). These values decreased slowly to approximately 6% and 22%, respectively, by 3 hours due to clearance of the perflubron emulsion from the circulation ($T_{1/2}=5$ hr, FIG. 6). Calculation of hemoglobin saturation (based on blood pH, temperature. $PCO_2$, and $PO_2$ levels), demonstrated that the percent of total oxygen consumption ($VO_2$) contributed by the hemoglobin-carried oxygen was significantly higher in the control dogs that in the perflubron emulsion-treated dogs (FIG. 7), indicating that the presence of the perflubron emulsion had a sparing effect on the reserve of $O_2$ still available in the red cells.

Although the invention has been described with reference to particular preferred embodiments, the scope of the invention is defined by the following claims and should be construed to include reasonable equivalents.

What is claimed is:

1. A method for facilitating autologous blood use by a patient facing a loss of blood, comprising the steps of:
   removing and maintaining a portion of the patient's blood;
   intravenously administering an effective oxygen delivery-enhancing amount of a synthetic biocompatible oxygen carrier;
   having said patient undergo a loss of blood subsequent to the administration of the oxygen carrier;
   administering breathing gas comprising 50%–100% oxygen to said patient during said loss of blood; and
   readministering said maintained blood to said patient.

2. The method of claim 1, further comprising the step of administering an effective cardiac output-increasing amount of a hemodiluent separately from said oxygen carrier in conjunction with said loss of blood.

3. The method of claim 2, wherein said hemodiluent is a crystalloid, colloid, or a combination thereof.

4. The method of claim 1, wherein the oxygen carrier is derived from human, animal, plant or recombinant hemoglobin.

5. The method of claim 1, wherein the oxygen carrier is a fluorocarbon emulsion.

6. The method of claim 1, wherein the amount of said oxygen carrier administered is no more than 3 g/kg, based on the body weight of the patient.

7. The method of claim 1, wherein said blood loss is associated with surgery.

8. The method of claim 7, further comprising the step of administering an additional amount of a biocompatible synthetic oxygen carrier to said patient during surgery.

9. The method of claim 1, wherein said blood loss is associated with trauma.

10. The method of claim 1, wherein said oxygen carrier further includes an effective cardiac output-increasing amount of a hemodiluent.

11. A method for facilitating autologous blood use by a patient facing a loss of blood, comprising the steps of:
    removing and maintaining a portion of the patient's blood;
    intravenously administering an effective cardiac output-increasing amount of a hemodiluent in conjunction with a surgical procedure involving a loss of blood;
    intravenously administering an effective oxygen delivery-enhancing amount of a synthetic biocompatible oxygen carrier in conjunction with said blood loss;
    administering breathing gas comprising 50%–100% oxygen to said patient during said loss of blood; and then
    readministering said maintained blood to said patient.

12. The method of claim 11, wherein said synthetic oxygen carrier is derived from human, animal, plant or recombinant hemoglobin.

13. The method of claim 11, wherein the oxygen carrier is a fluorocarbon emulsion.

14. The method of claim 11, wherein the amount of said oxygen carrier administered is no more than 3 g/kg, based on the body weight of the patient.

15. The method of claim 11, wherein said hemodiluent is a crystalloid, colloid, or a combination thereof.

16. The method of claim 11, further comprising the step of administering an additional amount of a biocompatible synthetic oxygen carrier to said patient during said surgical procedure.

17. A method for facilitating autologous blood use by a patient facing a loss of blood during surgery, comprising the steps of:
    removing and extracorporeally maintaining a portion of the patient's blood;
    intravenously administering a hemodiluent to said patient in conjunction with the removing step in a volume at least as great as the volume of blood removed, thereby increasing the cardiac output of the patient;

thereafter initiating a surgical procedure on said patient, said surgical procedure involving a loss of blood;

administering an effective oxygen delivery-enhancing amount, but no more than 3 g/kg, of a biocompatible synthetic oxygen carrier to said patient in conjunction with said surgical procedure; and administering a breathing gas to said patient during said surgical procedure, said breathing gas comprising 50%–100% oxygen.

18. The method of claim 17, wherein said synthetic oxygen carrier is a fluorocarbon in the form of a fluorocarbon emulsion.

19. The method of claim 17, wherein said synthetic oxygen carrier is hemoglobin.

20. The method of claim 17, further comprising the step of readministering said maintained blood to said patient.

* * * * *